(12) United States Patent
Hantash et al.

(10) Patent No.: US 8,323,253 B2
(45) Date of Patent: Dec. 4, 2012

(54) METHOD AND DEVICE FOR TIGHTENING TISSUE USING ELECTROMAGNETIC RADIATION

(75) Inventors: Basil M. Hantash, East Palo Alto, CA (US); Kin F. Chan, East Palo Alto, CA (US)

(73) Assignee: Reliant Technologies, Inc., Hayward, CA (US)

(*) Notice: Subject to any disclaimer, the term of this patent is extended or adjusted under 35 U.S.C. 154(b) by 1293 days.

(21) Appl. No.: 12/035,956

(22) Filed: Feb. 22, 2008

(65) Prior Publication Data

US 2008/0262482 A1 Oct. 23, 2008

Related U.S. Application Data

(60) Provisional application No. 60/891,422, filed on Feb. 23, 2007.

(51) Int. Cl.
*A61M 35/00* (2006.01)
*A61B 18/04* (2006.01)

(52) U.S. Cl. .......................... 604/290; 606/33
(58) Field of Classification Search ............ 604/289, 604/290; 606/9, 27, 41, 45, 49
See application file for complete search history.

(56) References Cited

U.S. PATENT DOCUMENTS

| | | |
|---|---|---|
| 6,997,923 B2 | 2/2006 | Anderson et al. |
| 7,372,606 B2 | 5/2008 | Broome et al. |
| 2005/0049582 A1* | 3/2005 | DeBenedictis et al. ........... 606/9 |
| 2005/0222555 A1 | 10/2005 | Manstein et al. |
| 2006/0004347 A1 | 1/2006 | Altshuler et al. |

OTHER PUBLICATIONS

PCT International Search Report and Written Opinion, PCT/US08/54753, Aug. 15, 2008, 11 pages.
Leffell, D., "Clinical Efficacy of Devices of Nonablative Photorejuvenation," Arch. Dermatol., Nov. 2002, pp. 1503-1508, vol. 138.

* cited by examiner

*Primary Examiner* — Melanie Hand
(74) *Attorney, Agent, or Firm* — Wood, Herron & Evans, LLP

(57) ABSTRACT

Methods and devices for treatment of skin are disclosed. These methods and devices use electromagnetic radiation to create networks or patterns of treatment zones. The networks or patterns of treatment zones comprise at least four treatment zones, at least two of the treatment zones in the network or pattern are slanted at angles in the skin, and the treatment zones extend at least as deep as the dermal-epidermal junction of the skin. Producing intersecting treatment zones and/or overlapping treatment patterns can increase the effectiveness of the treatments. The devices comprise a hand piece operably coupled to a delivery element, wherein delivery of electromagnetic radiation through the device to a portion of skin produces a network or pattern of treatment zones. The use of these methods and devices results in tightening of the skin and/or improvement in the cosmetic appearance of wrinkles in the portion of skin treated.

52 Claims, 9 Drawing Sheets

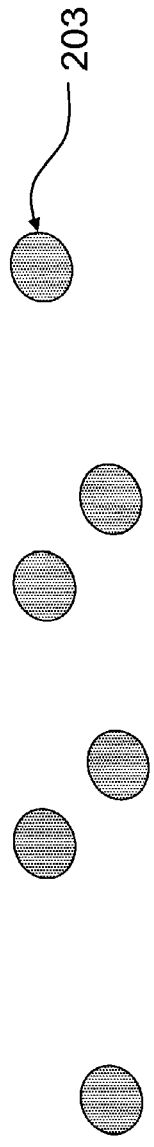
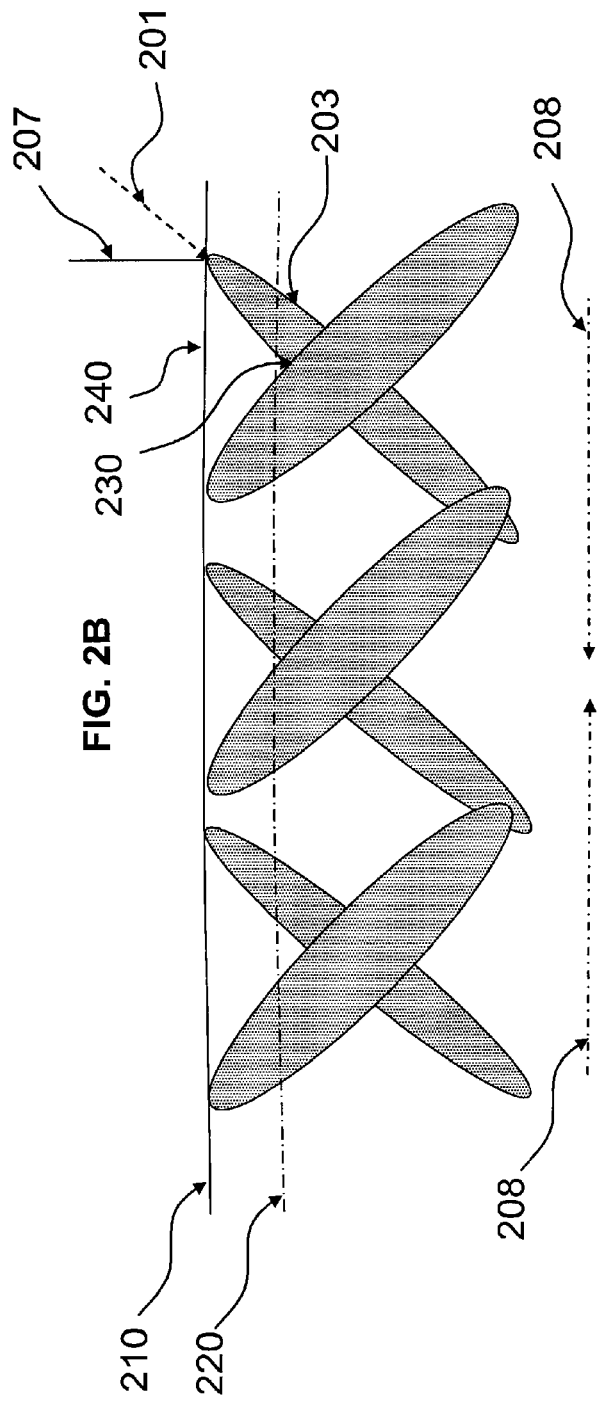

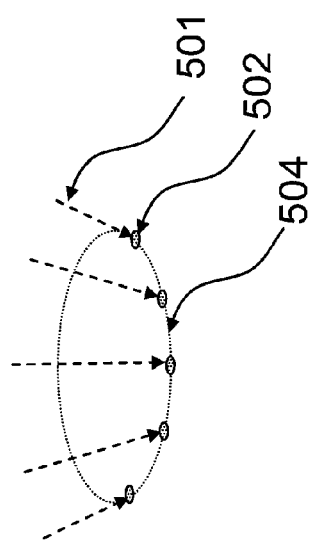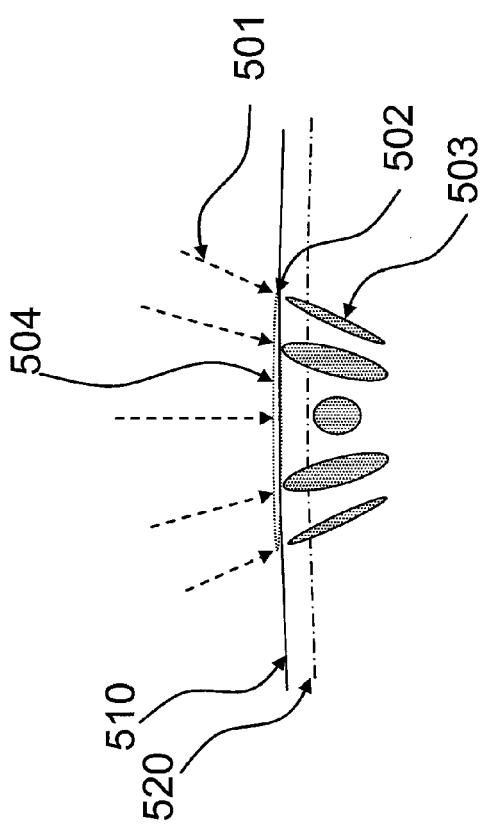
FIG. 5A
FIG. 5B

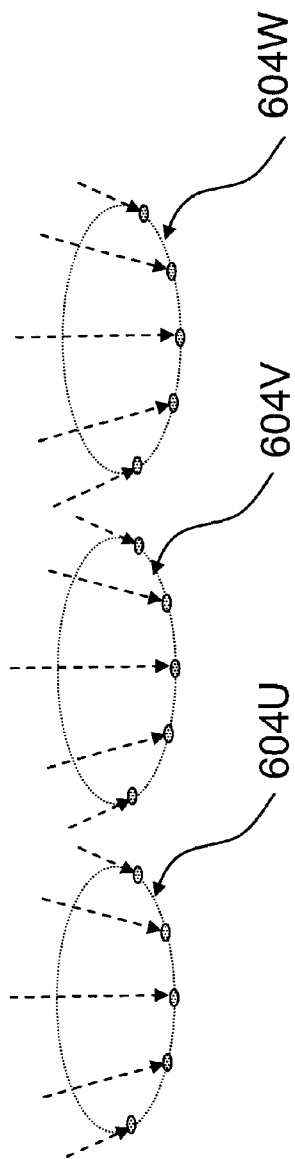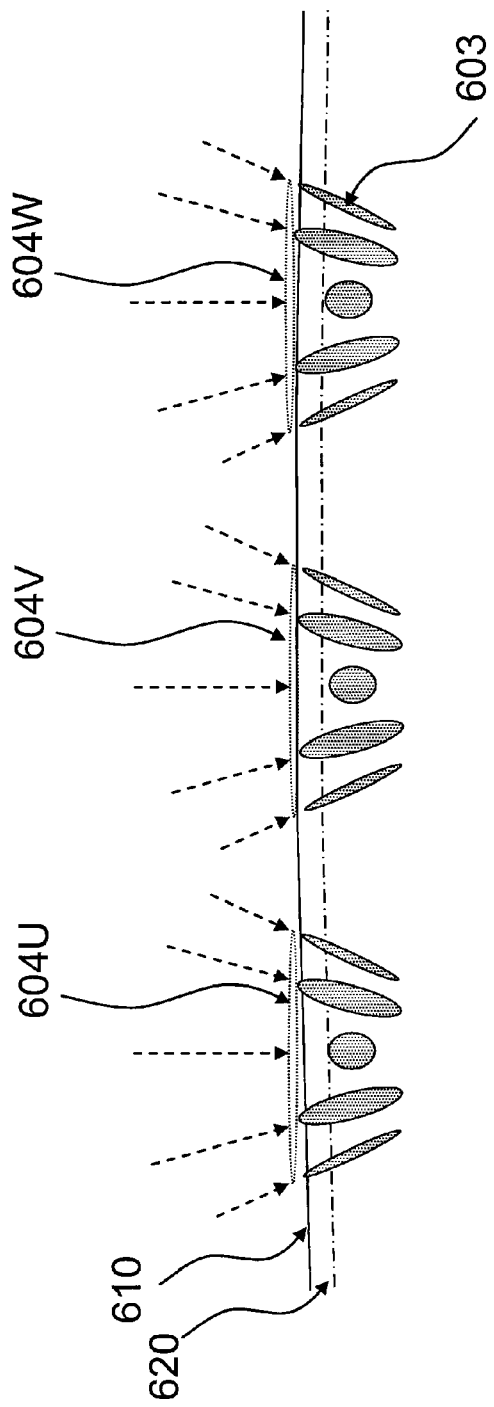

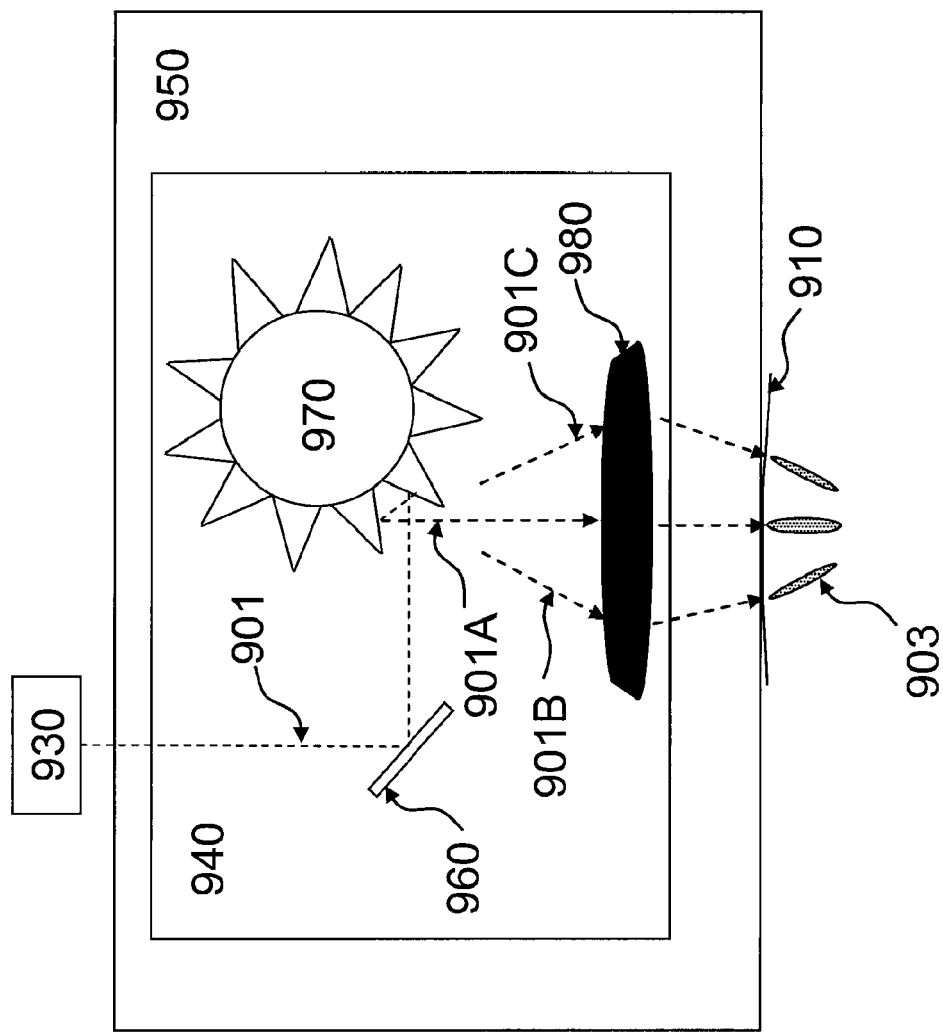

METHOD AND DEVICE FOR TIGHTENING TISSUE USING ELECTROMAGNETIC RADIATION

CROSS-REFERENCE TO RELATED APPLICATION

This application claims the benefit of U.S. provisional patent application Ser. No. 60/891,422 filed Feb. 23, 2007 under 35 U.S.C. 119(e), which is incorporated by reference in its entirety.

FIELD OF THE INVENTION

The present invention relates generally to methods and devices for providing cosmetic, medical or surgical treatments using electromagnetic radiation, and in particular to methods and devices for providing fractional treatments of tissue using electromagnetic radiation in a manner so as to tighten the tissue, particularly skin.

BACKGROUND OF THE INVENTION

Electromagnetic radiation, including ultraviolet radiation, visible light, infrared radiation, radar, and radio waves, has been applied directly to tissue, particularly skin, for many purposes, including for treatment of dermatological conditions, resurfacing, and to combat the effects of aging. Electromagnetic radiation can be coherent in nature, such as laser radiation, or non-coherent in nature, such as flash lamp radiation. Coherent electromagnetic radiation can be produced by lasers, including gas lasers, dye lasers, metal-vapor lasers, and/or solid-state lasers. Depending on the type of electromagnetic radiation (laser, flash lamp, radio frequency, etc.), the mode of usage (continuous wave or pulsed), and other parameters, such as the pulse width, the energy density and the power, different types of treatments and effects can be accomplished.

Electromagnetic radiation has been used to treat common dermatological problems, including hypervascular lesions, pigmented lesions, acne scars, rosacea, and hair removal. Electromagnetic radiation has also been used in aesthetic surgery to achieve better cosmetic appearances by resurfacing the skin and remodeling the different layers of skin, improving the appearance of wrinkled or aged skin. Generally, skin resurfacing is understood to be the process by which the top layers of the skin are completely removed using chemicals, mechanical abrasion or electromagnetic radiation to promote the development of new, more youthful looking skin and stimulate the generation and growth of new skin. For example, pulsed $CO_2$ laser skin resurfacing typically ablates the existing tissue to a layer below the papillary dermis, which can cause heat-induced coagulation to several hundred micrometers below the original skin surface. Following resurfacing, the tissue is regenerated and remodeled, producing skin with a better cosmetic appearance (i.e., improving photodamage, the appearance of wrinkles, acne scars, and other unwanted features).

A number of possible mechanisms may be responsible for the improvement of the appearance of the skin following resurfacing. Ablation and subsequent regeneration and remodeling of collagen through heat-induced collagen contraction may be involved. For example, in laser skin remodeling, the laser energy penetrates into the deeper layers of the skin and is aimed at altering and stimulating regeneration of the structure of extra-cellular matrix materials, such as collagen, that contribute to the youthful appearance of skin. Another possible mechanism which may lead to improvement in the appearance of skin is tightening of the skin through wound contraction which occurs as part of the normal wound healing process. Some studies have concluded that heat-induced collagen tightening is responsible for the long-lasting skin tightening produced by $CO_2$ laser skin resurfacing. (See, e.g., Fitzpatrick R E et al. (2000) Collagen Tightening induced by carbon dioxide laser versus erbium:YAG laser, Lasers Surg Med, 27(5):395-403).

Generally, the desired effects on the skin are thought to be accomplished by electromagnetic radiation-induced heating of the tissue. Induced heating for specific temperature and heating time combinations can result in thermal coagulation, cell necrosis, hemostasis, melting, welding, ablation and/or gross alteration of the extra-cellular matrix. When using electromagnetic radiation for skin resurfacing and/or remodeling, an important objective has been to provide uniform treatment across the desired treatment site. With such treatments, particular care is exercised, either by the physician alone or by combining the physician's judgment with intelligence that is built into the dermatological system, to leave no tissue untreated in the targeted region of the skin. Whether using a broadly radiating pulsed beam of radiation or a focused beam of radiation that produces a relatively smaller spot size, the goal has been to expose the entire treatment area to the electromagnetic radiation, in order to heat the entire volume of tissue in the treatment area and bring about the desired change. It has been widely reported that such broad area or bulk treatments result in undesirable side effects such as intolerable pain, prolonged erythema, swelling, occasional scarring, extended healing times, and infection.

Various forms of electromagnetic radiation, including laser radiation and radio frequency (RF) radiation, are increasingly being used for skin rejuvenation, including tightening the skin, particularly the skin of the facial area, to reduce the appearance of wrinkles and combat the effects of aging. Radiation sources frequently used for skin rejuvenation include $CO_2$ lasers, short pulsed Erbium:Ytrrium-Aluminum-Garnet (Er:YAG) lasers, combined $CO_2$/Er:YAG lasers, variable pulsed Er:YAG lasers, ablative radiofrequency devices, non-ablative lasers, and intense light sources. Of the commonly used treatments, resurfacing treatments using $CO_2$ lasers are generally considered to provide the most effective treatment for wrinkles and photoaging, as they produce the greatest degree of tightening of skin. (See, e.g., Goldberg D J, (2003) Lasers for facial rejuvenation, Am J Clin Dermatol 4(4):225-34). However, these bulk $CO_2$ laser treatments ablate large areas of the skin, cause dermal wounds, produce significant thermal effects within the treated tissue, and require long periods of time to heal—in many cases, up to a two week period of second-degree burn wound management and months of prolonged erythema.

Less aggressive treatments, such as lower energy or non-ablative lasers, while still effective in rejuvenating skin, typically produce fewer and less severe side effects and heal more rapidly. However, these less aggressive treatments typically do not produce as great of long-term improvements in tightening of skin and reduction in the cosmetic appearance of wrinkles as bulk $CO_2$ laser treatments. An objective of non-ablative skin rejuvenation is to induce a thermal wound repair response in the papillary and upper reticular layers of the dermis (approximately 100-400 micrometers below the surface of the skin) while sparing at least some cells at the junction between the dermal and epidermal layers of the skin. One approach used to achieve this objective is to spare the epidermal layer. To spare the epidermal layer, low fluences (laser energy densities) can be used. Unfortunately, such low levels are generally inadequate to promote the kinds of stimulation that is required to produce the desired tightening of the skin and reduction in the appearance of wrinkles. Thus, nonablative approaches can result in minimal efficacy. In most cases, minimal dermal matrix remodeling and minimal clinical responses (e.g., wrinkle reduction, retexturing, dyschromia reduction, and telangiectasia removal) are achieved by these procedures (See, e.g., Nelson et al, (2002) What is Nonablative Photorejuvenation of Human Skin, Seminars in Cutaneous Medicine and Surgery, 21:(4)238-250, 2002; Leffell D (2002) Clinical Efficacy of Devices of Nonablative Photorejuvenation, Arch. Dermatol. 138:1503-1508). Therefore, there is an unmet need for methods and devices which provide electromagnetic radiation treatments which spare the epidermal layer of the skin, but achieve enough stimulation of dermal matrix remodeling to be clinically effective in rejuvenating skin, tightening skin and treating wrinkles.

Various devices and approaches have been proposed to reduce the extent and duration of the side effects produced by treating tissue with electromagnetic radiation. One approach to minimize the effects of bulk heating of the skin is to cool the skin before, during or immediately following treatment, in an effort to reduce the level of thermal damage to the epithelium. While methods and systems such as these can reduce the damage to the skin during treatment, cooling systems pose practical limitations because of their added complexity. Another approach to sparing the epithelium includes systems that deliver electromagnetic radiation over a relatively large tissue surface area with the radiation focused in the dermis. Treatment methods such as these are designed to cover the target tissue in the plane of the skin completely with overlapping treatment zones so that no tissue in the treated portion of skin is left unexposed to electromagnetic radiation. However, by their nature, bulk treatment methods lead to an increase in clinical side effects and to an increase in healing time, and force physicians to lower the treatment intensity, resulting in less effective treatments.

When electromagnetic radiation at an effective treatment level is applied to tissue or skin, a burn or an acute wound is usually created. For acute wounds, the skin heals by three distinct 'response to injury' waves. The initial inflammatory phase has a duration lasting minutes to days, and seamlessly transitions into the cell proliferative phase, lasting 1 to 14 days. This cell proliferative phase is slowly replaced by the dermal maturation phase that lasts from weeks to months (See, e.g., Clark R (1999) Mechanisms of cutaneous wound repair. In: Fitzpatrick T B, ed. Dermatology in General Medicine, 5th Ed., McGraw-Hill, New York, N.Y. pp. 327-41).

In general, a direct correlation exists between the size of the injury and the time required for complete repair. However, the inflammatory phase is a function of cellular necrosis, particularly epidermal (i.e., keratinocyte) necrosis, and a direct correlation exists between cellular necrosis and the inflammatory phase. Increased cellular necrosis, particularly epidermal necrosis, prolongs the inflammatory phase. Prolonging and/or accentuating the inflammatory phase may be undesirable from a clinical perspective due to increased pain and extended wound repair, and may retard subsequent phases of wound repair. The cause(s) of this prolonged inflammatory phase are not well understood. However, injuries caused by electromagnetic radiation are associated with early and high levels of dermal wound repair (e.g., angiogenesis, fibroblast proliferation and matrix metalloproteinase (MMP) expression) but delayed epidermal resurfacing (See, e.g., Schaffer et al, (1997) Comparisons of Wound Healing Among Excisional, Laser Created and Standard Thermal Burn in Porcine Wounds of Equal Depth, Wound Rep Reg 5(1):51-61). Unfortunately, most of the skin resurfacing efforts and selective photothermolysis treatments that affect large contiguous areas of chromophores result in a prolonged, exaggerated inflammatory phase leading to undesirable consequences such as delayed wound repair. The prolonged inflammatory phase also leads to the pain experienced by most patients undergoing skin resurfacing procedures. Undesirable extended inflammatory response phase can be attributed to the bulk heating of the skin with little or no healthy tissue, particularly keratinocytes, left behind in the area where the skin was exposed to the electromagnetic radiation. Particularly when uniform treatment is desired and the entire target tissue volume is exposed to electromagnetic radiation without sparing any tissue within the target volume, pain, swelling, fluid loss, prolonged reepitheliazation and other side effects of dermatological laser treatments are commonly experienced by patients.

Increasingly, conventional bulk skin treatment methods are being replaced by various fractional treatment methods, as the use of fractional treatment methods has been found to produce fewer and less severe side effects than conventional bulk treatment methods, including reduced damage to the epidermal layers of the skin. Fractional treatment methods involve the generation of a large number of treatment zones within a region of tissue. The electromagnetic radiation impacts directly on only the relatively small treatment zones, instead of impacting directly on the entire region of tissue undergoing treatment, as it does in conventional bulk treatments. Thus, a region of skin treated using a fractional electromagnetic radiation treatment method is composed of a number of treatment zones where the tissue has been altered by the radiation, contained within a larger volume of tissue that has not been altered by the radiation. Fractional treatment methods make it possible to leave substantial volumes of tissue unaltered and/or viable within a treatment region.

Various fractional treatment methods have been used for treating both existing medical (e.g., dermatological) disease conditions and for improving the appearance of tissue (e.g., skin) by intentionally generating regions of thermally altered tissue surrounded by unaltered tissue. Fractional treatment methods generally offer numerous advantages over existing approaches in terms of safety and efficacy. Fractional treatment methods can reduce the undesirable side effects of pain, erythema, swelling, fluid loss, prolonged reepithelialization, infection, and blistering generally associated with laser skin resurfacing. By sparing healthy tissue around the thermally altered tissue, fractional treatment methods can increase the rate of recovery of the treatment zones by stimulating skin remodeling and wound repair mechanisms. Fractional treatment methods can also reduce or eliminate the side effects of repeated electromagnetic radiation treatments to tissue by controlling the extent of tissue necrosis due to exposure to electromagnetic radiation.

Among other approaches, U.S. Pat. No. 6,997,923 describes methods of treating a volume of a patient's skin by irradiating portions of the volume. The patent describes a method for performing a treatment on a volume located at area and depth coordinates of a patient's skin, the method involving providing a radiation source and applying radiation from the source to an optical system which concentrates the radiation to at least one depth within the area coordinates of the volume, the at least one depth and the selected areas defining three-dimensional treatment portions of the volume within untreated portions of the volume. The method is described as producing irradiated portions of tissue or treatment regions, where each irradiated portion is surrounded by a non-irradiated portion, and each treatment region is separated from other treatment regions by untreated tissue.

U.S. patent application Ser. No. 10/888,356 (US Patent Application Publication Number US 2005/049582) describes methods and apparatus for generating isolated, non-contiguous tissue volumes having treatment zones comprising necrotic tissue, surrounded by zones of viable tissue that are capable of promoting healing of the target tissue. Specifically, the application describes creating a plurality of microscopic treatment zones in a predetermined treatment pattern, wherein a subset of the plurality of discrete microscopic treatment zones includes discrete microscopic treatment zones comprising necrotic tissue volumes having an aspect ratio of at least about 1:2.

U.S. patent application Ser. No. 11/097,825 (US Patent Application Publication Number US 2005/0222555) describes apparatus and methods for treating skin by providing a skin damaging means and applying the skin damaging means to create a plurality of micro-lines of damaged tissue in a region of skin separated by regions of undamaged skin tissue, wherein the micro-lines are substantially parallel and traverse at least part of said region of skin being treated. The application defines 'micro-lines' as narrow regions of damaged dermal tissue, generally less than 1 mm in width, that extend from the surface of the skin into the epidermis and, optionally, through the epidermis and into the dermal layer. The micro-lines are long in one direction along the surface of the skin, generally at least four to five times as long as the width of the micro-lines, and may traverse part or all of the region of skin being treated.

U.S. patent application Ser. No. 11/098,036 (US Patent Application Publication Number US 2006/0004347) describes devices, systems and methods of treatment of tissue with electromagnetic radiation (EMR) to produce lattices of EMR-treated islets in the tissue. The islets are described as being separated from each other by non-treated tissue (or differently- or less-treated tissue), and numerous advantages are attributed to the production of lattices of EMR-treated islets in the tissue rather than large, continuous regions of EMR-treated tissue.

These treatment methods can be suitable for treating skin to achieve a better cosmetic surface by resurfacing the skin and remodeling the layers of skin to improve the appearance of wrinkled or aged skin while avoiding extensive damage to the epithelial layer of the skin. Using these treatment methods can produce small to moderate increases in tightening of the skin and the cosmetic appearance of wrinkles due to shrinkage of collagen fibrils subjected to elevated temperature or coagulation of localized areas in the dermis and hypodermis. However, the level of improvement in skin tightening and the appearance of wrinkles achieved using these treatment methods appears to be less than the level of improvement achieved using bulk ablative treatments, such as conventional pulsed $CO_2$ laser skin resurfacing. A need remains in the art for methods of treatment and devices which provide the benefits of fractional electromagnetic radiation treatment methods while achieving significant increases in skin tightening and the appearance of wrinkles more comparable to those produced by bulk electromagnetic radiation treatment methods and devices.

SUMMARY OF THE INVENTION

Methods and devices are disclosed for treating skin by using electromagnetic radiation to create networks or patterns of treatment zones in a portion of skin. The devices comprise a handpiece operably coupled to a delivery element, wherein delivery of electromagnetic radiation through the device to a portion of skin produces a network or pattern of treatment zones. The networks or patterns of treatment zones contain at least four treatment zones, of which at least two of the treatment zones are slanted at angles in the portion of skin, and the treatment zones extend at least as deep as the dermal-epidermal junction of the portion of skin. Producing intersecting treatment zones and/or overlapping treatment patterns can increase the effectiveness of the treatments. The use of these methods and devices results in tightening of the skin and/or improvement in the cosmetic appearance of wrinkles in the portion of skin treated. These methods and devices can be used to provide cosmetic, medical and/or surgical treatments to tissue.

In one example, the method for treating skin comprises treating a portion of skin with electromagnetic radiation in a manner so as to create a network of treatment zones in the portion of skin, wherein the network comprises at least four treatment zones, at least two of the treatment zones in the network are slanted at angles in the portion of skin, the treatment zones extend at least as deep as a dermal-epidermal-junction of the portion of skin, at least one of the treatment zones in the network intersects another treatment zone in the network, the treatment zones intersect at a point below an epidermal layer of the portion of skin, and the treating results in tightening of the portion of skin. In another example, the treating results in an improvement in the cosmetic appearance of wrinkles in the treated portion of skin. In another example, the treatment zones intersect at a point below the dermal-epidermal junction of the portion of skin. In yet another example, the skin substantially perpendicularly above the point at which the treatment zones intersect is not treated.

In another example, the method for treating skin comprises treating a portion of skin with electromagnetic radiation in a manner so as to produce a pattern of treatment zones in the portion of skin, wherein the pattern comprises at least four treatment zones, at least two of the treatment zones in the pattern are slanted at angles in the portion of skin, the treatment zones extend at least as deep as a dermal-epidermal-junction of the portion of skin, and the treating results in tightening of the portion of skin. In another example, the treating results in an improvement in the cosmetic appearance of wrinkles in the treated portion of the skin. In another example, a first treatment pattern is at least partially overlapped with a second treatment pattern. In another example, at least partially overlapping the first and second treatment patterns causes at least one treatment zone in the first pattern to intersect a treatment zone in the second pattern. In yet another example, at least two of the treatment zones in the pattern are slanted at angles such that lines projected along the length of each treatment zone intersect at substantially a single point below a surface of the portion of skin, wherein the treatment zones do not extend as deep as the point and do not intersect.

In one example, the device for treating skin comprises a hand piece operably coupled to a delivery element, wherein delivery of electromagnetic radiation through the device to a portion of skin produces a network of at least four treatment zones, at least two of the treatment zones are slanted at angles in the portion of skin, the treatment zones extend at least as deep as the dermal-epidermal junction of the portion of skin, and at least one of the treatment zones in the network intersects another treatment zone in the network. In another example, the treatment zones intersect at a point below the epidermal layer of the skin. In another example, the treatment zones intersect at a point below the dermal-epidermal junction of the portion of skin. In yet another example, the skin substantially perpendicularly above the point at which the treatment zones intersect is not treated.

In another example, the device comprises a hand piece operably coupled to a delivery element, wherein delivery of electromagnetic radiation through the device to a portion of skin produces a pattern of at least four treatment zones, at least two of the treatment zones are slanted at angles in the portion of skin, and the treatment zones extend at least as deep as a dermal-epidermal junction of the portion of skin. In another example, all the treatment zones in the pattern are slanted at angles in the portion of skin. In yet another example, the slanted treatment zones in the pattern are slanted at angles such that lines projected along the length of each slanted treatment zone intersect at substantially a single point below an epidermal layer of the portion of skin, wherein the treatment zones in the pattern do not extend as deep as the point and do not intersect.

Other aspects of the invention include methods corresponding to the devices described above.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 2 consists of two drawings, a top-view (FIG. 2A) and a cross-sectional view (FIG. 2B) illustrating a series of intersecting slanted treatment zones which form a treatment network.

FIG. 5 consists of two drawings, a perspective view (FIG. 5A) and a cross-sectional view (FIG. 5B) showing a treatment pattern of five beams of electromagnetic radiation impacting a portion of skin.

FIG. 6 consists of two drawings, a perspective view (FIG. 6A) and a cross-sectional view (FIG. 6B) showing three treatment patterns, each containing five beams of electromagnetic radiation, impacting a portion of skin. The three treatment patterns in FIG. 6 are not overlapped.

FIG. 9 is a cross-sectional drawing illustrating a device for treating skin which uses a galvanometer scanner and a starburst scanner to deflect a beam of electromagnetic radiation in two dimensions, creating a network and/or pattern of treatment zones in a portion of skin.

DETAILED DESCRIPTION OF THE PREFERRED EMBODIMENTS

As used in the specification and the appended claims, the singular forms "a," "an" and "the" include plural referents unless the context clearly dictates otherwise.

"Tissue" refers to an aggregate of cells that perform specific functions, including but not limited to muscle, organs, and the skin, including the epidermis, dermis and subcutis. The cells of a tissue may or may not form a layer.

"Treatment zone" refers to a region of tissue within a larger volume of tissue which receives an effective amount of electromagnetic radiation. Thus, when a region of tissue is treated with electromagnetic radiation in a fractional manner, the region of tissue will contain a plurality of treatment zones to which electromagnetic radiation was directed, surrounded by regions to which electromagnetic radiation was not directed. Treatment zones can be created independently or more than one treatment zone can be created simultaneously or effectively simultaneously. A number of treatment zones can be created in a network or pattern, and the network or pattern can be repeated and/or overlapped within a portion of skin. Depending upon the treatment method and/or method of delivering the electromagnetic radiation used, a treatment zone can be comprised of tissue that has been ablated, necrosed, coagulated, melted, welded, and/or had its extra-cellular matrix grossly altered in some manner. Also depending upon the treatment method and/or method of delivering the electromagnetic radiation used, treatment zones may or may not intersect other treatment zones (i.e., may or may not be separate or discrete).

"Tightening" as used herein is synonymous with contracting, shrinking, constricting and pulling together tissue, either in a horizontal, vertical or angular direction.

Figure 1:
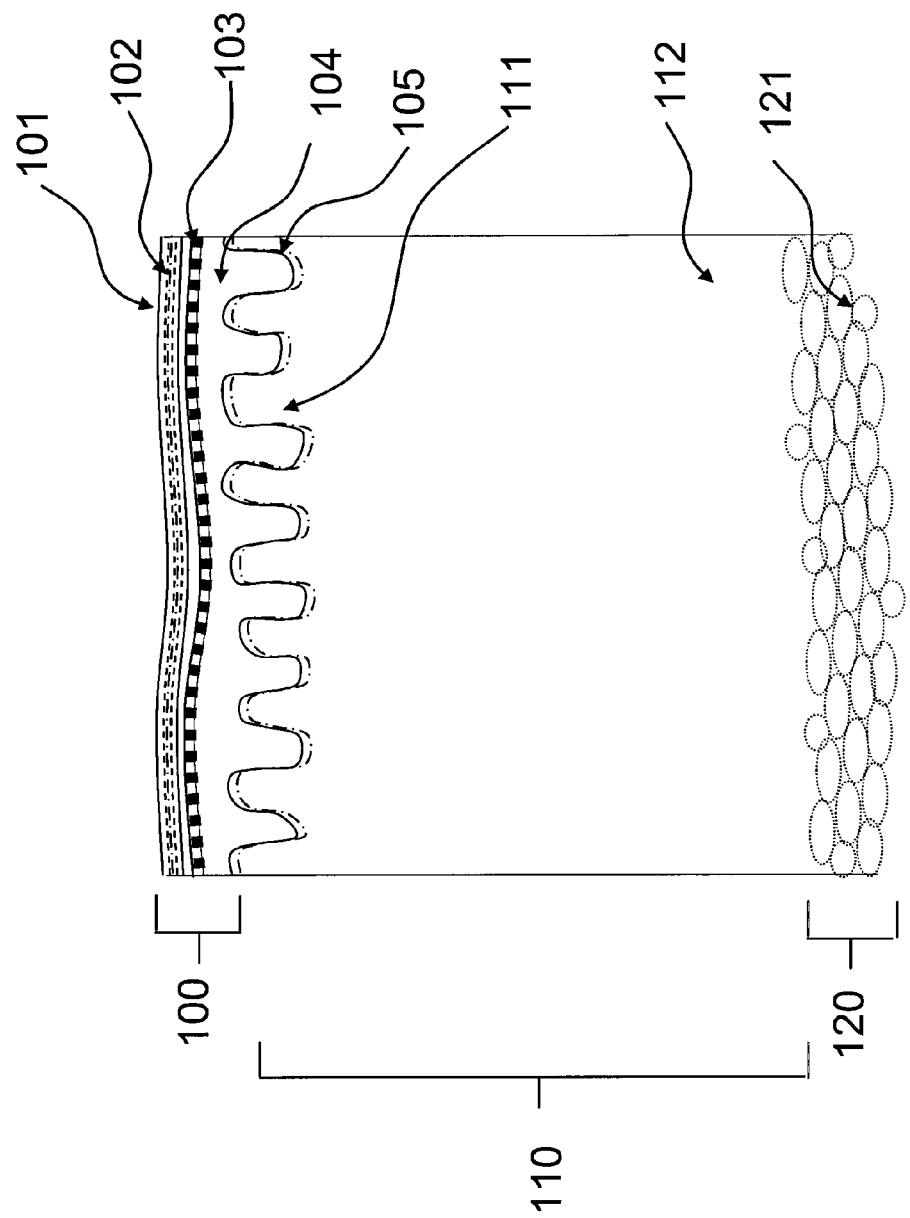
FIG. 1 is a cross-sectional drawing illustrating the layers of the skin.

The drawing in FIG. 1 illustrates the basic structure of the skin, the body's outer covering. The skin is composed of three principal layers, the epidermis (100), dermis (110) and subcutis (120). The epidermis comprises the upper or outer layers of the skin, is nonvascular, and varies in thickness over different parts of the body. The epidermis itself is composed of several different layers, specifically the stratum corneum (101), stratum lucidum (102), stratum granulosum (103), stratum spinosum (104), and stratum basale (105) layers.

Skin is a multilayered heterogenous tissue composed of superimposed layers that are intimately connected but very distinct in their nature, structure and properties. The top layer is the epidermis, which is between about 0.06 mm and about 1.0 mm thick and is composed of five distinct layers: the stratum corneum (101), the stratum lucidum (102), the stratum granulosum (103), the stratum spinosum (104), and the stratum basale (105). The epidermis is connected to the lower layer, the dermis, which is between about 1 mm and about 4 mm thick and is composed primarily of cells and extra-cellular matrix. The dermis can be further subdivided into the papillary dermis and reticular dermis layers. (See, e.g., Reihsner R et al. (1995) Two-dimensional elastic properties of human skin in terms of an incremental model at the in vivo configuration, Med. Eng. Phys., 17(4):304-313; Silver F et al. (2003) Mechanobiology of force transduction in dermal tissue, Skin Research and Technology 9:3-23.)

The uppermost or outermost layer of the skin is the stratum corneum (101), also known as the "horny layer" of the skin. The cells within the stratum corneum are flat and scale-like in shape and hydrophobic in nature. These dead, non-nucleated cells, composed mainly of the protein keratin, are arranged in overlapping, often peeling layers with naturally interspersed pores.

Below the stratum corneum (101) is the stratum lucidum (102), a homogeneous translucent band, much thinner than the layers above and below it. Below the stratum lucidum (102) layer of the epidermis is the stratum granulosum (103), composed of two or three rows of flat cells composed mainly of keratohyalin, which is transformed into keratin in more superficial layers. Below the stratum granulosum (103) is the stratum spinosum (104), composed of several layers of polygonal cells known as "prickle cells". The number of layers of cells in the stratum granulosum varies over different regions of the body. Below the stratum spinosum (104) layer is the stratum basale (105) layer, also known as the stratum germinativum, the deepest layer of the epidermis. The stratum basale is composed of columnar cells which are continually dividing to produce new skin cells. It is the cells in the stratum basale that produce melanin. Over time, the cells produced in the stratum basale move upward and away from the blood supply, and their cell contents and shapes change, forming the different layers of the epidermis. The dermal-epidermal junction is the region of the skin in which the bottom layer of the epidermis (the stratum basale (105)) and the top layer of the dermis (the papillary dermis (111)) join.

The dermis (110) is the inner layer of the skin containing blood capillaries, blood vessels, lymph vessels, hair follicles, and various glands, including eccrine sweat glands and sebaceous glands. The dermis is composed of felted connective tissue containing elastin, collagen and fat. The dermis is divided into the upper, papillary layer (111) and the lower, reticular layer (112). The papillary layer (111) of the dermis typically contains a large number of dermal papillae which rise perpendicularly from its surface. The papillary layer (111) of the dermis also contains blood capillaries which carry nutrients to, and remove waste from, the dividing cells in the stratum basale (105). The reticular layer (112) of the dermis typically contains veins, arteries, sebaceous glands, arrector pili muscles, sensory nerve fibers, hair follicles, hair roots, pacinian corpuscles, hair root plexus, and eccrine sweat glands.

At the base of the dermis lies the subcutis (120), also known as the hypodermis or superficial fascia, which separates the dermis from the underlying muscle and is composed primarily of adipose tissue (121).

The mechanical properties of skin reflect the passive behavior of the elastin and collagen fibers in the dermis, as well as an active component reflecting keratinocyte-keratinocyte, fibroblast-fibroblast, and fibroblast-extracellular matrix interactions. While collagen is the main source of strength and stiffness of skin, elastin fibers forming a scattered delicate network between the collagen fibers are thought to be primarily responsible for the recoiling mechanism after a stress or deformation has been applied. Aging produces major changes in skin's mechanical properties. These changes are thought to be due to increased crosslinking of collagen fibers, the degradation of the elastin network, and age-dependent changes in the ground substance which alter the viscoelastic properties. (See, e.g., Reihsner R et al (1995); Silver F et al. (2003)).

A state of tension exists naturally in the skin. For example, wounded skin will gape, becoming elliptical instead of round. A number of researchers have identified and characterized different cleavage or tension lines in the skin (e.g., Langer's cleavage lines, Kraissl's lines, Borges' relaxed skin tension lines (RSTL), etc.) which can be followed when making surgical incisions to try to minimize the appearance of scars. Relaxed skin tension lines are usually perpendicular to the underlying muscle, and do not necessarily correlate with wrinkle lines. Borges' lines are considered by some surgeons to be the best guide for elective incisions on the face, while Kraissl's lines are considered the best guide for the rest of the body. On the face, Borges' RSTL follow furrows formed when the skin is relaxed. They are not visible features of the skin, as are wrinkles. Borges' lines are derived from the furrows produced by pinching the skin; fewer and higher furrows are produced when pinching skin parallel to the lines. Borges' lines are almost perpendicular to Langer's lines in the areas of the scalp, forehead, glabella, mid-cheek, and lateral eye. (See, e.g., Wilhelmi B (1999) Langer's Lines: To Use or Not to Use, Plastic and Reconstructive Surgery 104(1):208-214)

In the skin, external forces are transmitted through the epidermis to the dermis and the underlying subcutaneous tissues, while internal forces are transmitted through the dermis to the epidermis. Internal forces in the skin exist as passive tension in the collagen fibrils of the dermis running almost parallel to the Langer's lines and are augmented by active cytoskeletal tension. Tension in the epidermis has been speculated to lead to stretching of the basal epithelial cell junctions, resulting in tension at the dermal-epidermal junction. The active cellular tension also acts approximately along the Langer's lines and is produced by fibroblast contraction of collagen fibrils in the extra-cellular matrix. In the absence of external forces, the internal tension acting on the collagen fibrils of the dermis cause tension to occur at keratinocyte-keratinocyte cell junctions. External forces applied to the skin surface at the air-epidermis interface also increase the tension at keratinocyte-keratinocyte cell junctions as well as change the state of stress in the dermis. Transmission of external forces through the epidermis to the dermis occurs through a number of possible mechanisms, including: keratinocyte-keratinocyte interactions in the epidermis, keratinocyte-extracellular matrix interactions at the dermal-epidermal junction, macromolecular-macromolecular interactions in the dermis, and fibroblast-fibroblast interactions in the dermis. It has been noted that the mechanical continuity of the dermal-epidermal junction, as well as between the keratinocytes, is key to normal transfer of internal and external mechanical forces between the epidermis and dermis. It has also been noted that the internal forces in the dermis are larger than those in the epidermis, and that the epidermis can be stretched due to tension transmitted from the underlying dermis (See, e.g., Silver F et al. (2003)).

As previously discussed, electromagnetic radiation is frequently used to treat skin so as to tighten the skin and/or reduce the cosmetic appearance of wrinkles. While conventional bulk treatment methods and devices have been used to ablate or coagulate tissue as deep as the dermis, the complete ablation or coagulation of skin in the treated region has made it impossible to create a treatment at an angle in the skin, or assess the impact of treatment angle or treatment depth on the effectiveness of the treatment. However, the advent of fractional treatment methods and devices has let to the ability to control both the angle of treatment zones in the skin and their depth. The advent of fractional treatment methods and devices also make it possible to create networks or patterns of treatment zones, and to orient these networks or patterns in particular directions based on skin features such as Langer's lines, Borges' lines, Kraissl's lines, resting skin tension lines, wrinkles, etc.

A primary aspect of methods and devices described herein is the fractional nature of the treatments, which involves the sparing of volumes of tissue within a larger tissue treatment area. By leaving healthy tissue between and around the treatment zones, a number of beneficial effects are produced. If the treatment zones, networks and/or patterns are appropriately spaced and/or epidermal injury is limited, the viable tissue bordering the treatment zones will be subjected to less inflammation from the products of cell death, thereby favoring cell survival over apoptosis. These areas will be better able to mount reepithelialization and fibro-proliferative and subsequent remodeling phases of wound repair. One important reason for this effect is that the treatment zones and the bordering spared tissue contain subpopulations of stem cells responsible for repopulating the epidermis (See, e.g., Watt F (2002) The Stem Cell Compartment in Human Interfollicular Epidermis, J. Derm. Sci., 28:173-180). In humans, stem cells reside in two locations in the skin: in focal clusters in the stratum basale, and in the follicular bulge area surrounding hair shafts. The stratum basale layer of the epidermis typically contains a low population of these stem cells interspersed with large numbers of transit-amplifying (TA) cells that are directly derived from stem cells. Interfollicular epidermal stem cells tend to cluster at the bases of rete ridges in acral areas and at the tips of dermal papillae in non-acral skin. The follicular stem cell compartment has been shown to possess the ability to re-populate the interfollicular epidermal surfaces when required under certain conditions. Such conditions include severe burns, large split-thickness epidermal injuries, and cosmetic surgical procedures (e.g., ablative laser resurfacing, chemical peels, dermabrasion, keratotomy, etc.) that denude the epidermal layer, leaving no epidermal stem cell populations. It is well known that $CO_2$ resurfacing results in prolonged reepithelialization when compared to steel scalpel or electrosurgical scalpel incisions, even though laser wounds exhibit accelerated dermal healing (See, e.g., Schaffer et al., (1997) Comparisons of Wound Healing Among Excisional, Laser Created and Standard Thermal Burn in Porcine Wounds of Equal Depth, Wound Rep Reg 5(1):51-61). Reepithelization to repair such defects is delayed under these circumstances, because healing must occur from remaining follicular stem cell populations within the de-epidermized wound and from epithelial stem cells at the margins of the defect. If the wound is full thickness, extending down to the level of the pilosebaceous unit, then healing is delayed even further because epidermal healing occurs only from the margins.

By creating isolated, non-contiguous (i.e., discrete) treatment zones having coagulated and/or necrotic tissue surrounded by zones of viable (i.e., heat altered but viable tissue and/or untreated, un-altered healthy tissue) tissue that are capable of promoting healing, fractional treatment methods induces multiple sites of tissue regeneration. Following fractional treatment, a treated portion of tissue is typically composed of thousands of treatment zones that comprise "nodes" of wound repair. The healing mechanisms (e.g., stem cells and TA cells) of each node can be expected to expand beyond the volume of the node to merge with neighboring nodes, replacing photo-aged tissue components (e.g., solar elastosis, microvascular ectasia, pigment incontinence, epidermal atrophy, and atypia).

Fractional electromagnetic radiation treatment methods do not treat the entire volume of tissue in a region undergoing treatment. Not treating the entire volume of the tissue with electromagnetic radiation, but instead treating only a fraction of the tissue permits the retention of viable tissue between treatment zones. In some cases, electromagnetic radiation treatment parameters can be chosen which produce fractional treatments that spare the outermost layers of the epidermis, such as, for example, the stratum corneum, from significant damage. Such sparing of the stratum corneum promotes healing by maintaining the structural integrity and protective character of the stratum corneum. Fractional treatments are fundamentally different from bulk techniques because the areas of epidermal tissue that remain untreated between treatment zones contain both epidermal stem cells and TA cell populations. Thus, re-epithelization of treatment zones proceeds rapidly with few or none of the side effects (i.e., pain, persistent erythema, edema, fluid drainage, etc.) observed after bulk resurfacing procedures. By using small treatment zone cross-sections (e.g., for circular cross sections, less than about 500 micrometers in diameter, less than about 250 micrometers in diameter, or less than about 100 micrometers in diameter), significant numbers of stem cells and TA cells are relatively close to the center of the treatment zone throughout the depth of the treatment zone. This further speeds the healing response, such that substantially complete (e.g., greater than about 75% complete) re-epetheliazation typically occurs in less than about 36 hours post-treatment for treatment zones with cross-section widths in the range of less than about 250 micrometers. For treatment zones with cross-sectional widths of less than about 100 micrometers, substantially complete re-epetheliazation occurs less than about 24 hours post-treatment. Re-epetheliazation typically occurs at a rate corresponding to the cross-sectional width of the treatment zone. As a further example, if the spacing between fractional beam treatment zones creates an average density (i.e., number of treatment zones per unit surface area of the target treatment area) of 500 treatment zones/cm², there are ample epidermal stem cells that remain for interfollicular resurfacing of the treatment zone. In addition, after many types of fractional treatments with electromagnetic radiation, the follicular bulge stem cell population remains intact, so they may participate in wound healing and resurfacing, as needed. The density of treatment can be described using a fill factor (i.e., surface area receiving radiation divided by total surface area of the target treatment area), wherein a typical fill factor can be between about 0.05 and about 0.95, or between about 0.1 and about 0.5. The density of treatment can alternately be described using density (i.e., the number of treatment zones produced per surface area treated), wherein a typical treatment zone (TZ) density can be between about 50 TZ/cm² and about 6000 TZ/cm² or between about 200 TZ/cm² and about 2000 TZ/cm².

The methods of treatment and devices described herein provide the benefits of fractional electromagnetic radiation treatment methods while also producing significant levels of skin tightening and/or improvement in the appearance of wrinkles. These methods and devices can be used for cosmetic as well as non-cosmetic purposes. These methods of treatment and devices can be used on other tissues in addition to skin. These treatment methods and devices, instead of creating a multiplicity of isolated, non-contiguous, parallel treatment zones substantially perpendicular to the surface of the skin, create a multiplicity of treatment zones, a proportion of which are slanted at angles in the portion of skin.

Networks or patterns of at least four treatment zones, wherein the networks or patterns contain at least two slanted treatment zones can be produced. In some cases, between about 0.5% and about 100% of the treatment zones in the network or pattern are slanted. In other cases, between about 25% and about 90% of the treatment zones in the network or pattern are slanted. In other cases, between about 50% and about 85% of the treatment zones in the network or pattern are slanted. In some cases, the networks of treatment zones can contain intersecting treatment zones. In some cases, between about 0.5% and about 100% of the treatment zones in the network or pattern intersect at least one other treatment zone in the network or pattern. In other cases, between about 25% and about 90% of the treatment zones in the network or pattern intersect at least one other treatment zone in the network or pattern. In other cases, between about 50% and about 85% of the treatment zones in the network or pattern intersect at least one other treatment zone in the network or pattern. In some cases, the patterns of treatment zones can be at least partially overlapped, which can produce intersecting treatment zones. In some cases, the patterns are overlapped between about 0.5% and about 95%. In other cases, the patterns are overlapped between about 25% and about 90%. In other cases, the patterns are overlapped between about 50% and about 85%.

The treatment zones, both those substantially perpendicular to the surface of the skin and those slanted at angles in the skin, penetrate at least as deep as the dermal-epidermal junction of the portion skin. Methods of treatment and devices which produce these networks or patterns containing slanted treatment zones can be used to tighten skin and/or improve the cosmetic appearance of wrinkles in the treated portion of skin. Producing networks of intersecting treatment zones increases the treatment effects, as does producing patterns of at least partially overlapping, and, in some cases, intersecting, treatment zones.

Use of the treatment methods and devices described herein results in the creation of a multiplicity of treatment zones containing coagulated and/or necrosed tissue within a portion of skin. Tension in the coagulated and/or necrosed tissue shrinks the tissue, thereby tightening the skin. The wound-healing response, which is enhanced by adjacent viable tissue surrounding the treatment zones, causes replacement of the coagulated and/or necrosed tissue with new viable tissue, further tightening the tissue and enhancing skin elasticity. Creating treatment zones which are slanted at angles in the portion of skin can increase the shrinkage of the tissue, producing increased levels of skin tightening. It can also create an anisotropic shrinkage of the tissue as a whole. Creating networks or patterns containing slanted treatment zones and/or creating intersecting treatment zones can further increase the shrinking of the tissue, again increasing tightening of the skin and reducing the appearance of wrinkles.

Depending upon the treatment parameters used, the treatment can ablate, necrose, coagulate, melt, weld, and/or grossly alter the extra-cellular matrix of the tissue within the treatment zones. Sufficiently raising the temperature of collagen in the treatment zones can result in dramatic shrinkage or shortening of the collagen fibers, creating a region of contractile tissue within each of the treatment zones. In cases where the treatment results in ablation within the treatment zone, the contractile tissue rapidly shrinks the ablated void. In cases where the treatment results in coagulation and/or necrosis, the contractile tissue creates an increase in skin tension, resulting in a prompt reduction of overall skin laxity and the appearance of wrinkles. Upon collagen shrinkage due to coagulation, the dermal tissue is pulled inward, effectively tightening the dermal tissue. This tightening due to collagen shrinkage pulls taut any overlying laxity through a stretching of the epidermis and stratum corneum. Treatment zones created substantially perpendicular to the skin surface pull the dermal tissue up in the vertical direction, from top to bottom. Treatment zones which are slanted at angles within the skin, however, pull the dermal tissue up and sideways, adding horizontal or side-to-side tension to the vertical tension, which increases the skin tightening effects. The skin tightening effect of collagen shrinkage is primarily due to the connection of the basement membrane region of the epidermis to the collagen and elastin extra-cellular matrix, which provides a link between the epidermis and the dermis. Slanting the treatment zones at angles within the skin increases the surface area over which this link is created, and increases the side-to-side tension in the tissue. One theory for the high levels of skin tightening produced by conventional bulk $CO_2$ laser skin treatments is that these treatments have a significant effect on a large portion of dermal tissue. Producing slanting treatment zones increases the amount of dermal tissue impacted by the treatment while sparing the epidermal layers of the skin from excessive damage. Intersecting the slanted treatment zones below the epidermis (i.e., at or below the dermal-epidermal junction) produces a larger region of dermis that is linked to a given region of epidermis, further increasing skin tightening Producing slanting treatment zones which intersect below the dermal-epidermal junction, or avoiding treatment of the skin perpendicularly above a point of intersection, spares the epidermis from receiving the most damaging treatments (i.e., being treated two times at the same spot). Sparing the epidermis while more substantially treating the dermis not only reduces the down-time and side effects of the treatment, but also increases the positive skin-tightening effects.

Networks of treatment zones containing treatment zones that are slanted at angles in the skin can be used to increase and control the direction of the tension produced in the skin by the treatment. Additionally, producing intersecting treatment zones can further increase the tension, as regions of collagen shrinkage become linked to other regions of collagen shrinkage and further increase tension. Patterns of treatment zones containing treatment zones that are slanted at angles in the skin can also be used to increase and control the direction of the tension produced in the skin. For example, producing a pattern of treatment zones where the slanted treatment zones are along lines focused at a single point, but where the treatment zones do not converge at that point, can produce tension which 'pulls' the skin toward that point.

Additionally, treatment networks or patterns can be oriented based on skin features such as Langer's lines, Borges' lines, Kraissl's lines, resting skin tension lines, lines of maximum extensibility, wrinkles, underlying muscles, etc. This can result in collagen being laid down preferentially in a desired direction during the healing process, and/or in tightening of skin in a desired direction. For example, orienting the treatment networks or patterns along the same axis as a skin feature (e.g., along the long axis of a wrinkle) can help to produce a treatment that at least partially counteracts the natural tension of the wrinkle by tightening the skin perpendicular to the wrinkle, thereby stretching and minimizing the wrinkle. In one example, the treatment networks or patterns can be made parallel with the skin feature. In another example, the treatment networks or patterns can be made perpendicular with the skin feature. In yet another example, the treatment networks or patterns can be made at an angle of between about 10 degrees and about 85 degrees with the skin feature. Additionally, bandages or sutures can be applied to stretch the skin and/or increase the tension in a desired direction during the healing process.

The collagen shrinkage mechanism within the treatment zones is further supplemented by the wound healing process. The columns of coagulated tissue created in each of the treatment zones have excellent mechanical integrity that supports a progressive remodeling process without significant loss of the original shrinkage. In addition, the coagulated tissue acts as a tightened tissue scaffold with increased resistance to stretching. This further facilitates wound healing and skin tightening. The tightened scaffold serves as the structure upon which new collagen is deposited during wound healing and helps to create a significantly tighter and longer lasting effect.

In one example, a method for treating skin comprises: treating a portion of skin with electromagnetic radiation in a manner so as to create a network of treatment zones in the portion of skin, wherein the network comprises at least four treatment zones, at least two of the treatment zones in the network are slanted at angles in the portion of skin, the treatment zones extend at least as deep as a dermal-epidermal junction of the portion of skin, at least one of the treatment zones in the network intersects another treatment zone in the network at a point below an epidermal layer of the portion of skin, and the treating results in tightening of the portion of skin.

In one example, the network comprises at least twenty treatment zones. In another example, the network comprises at least fifty treatment zones. In yet another example, the network has a treatment zone density of between about 50 treatment zones (TZ) per square centimeter and about 2000 TZ/cm$^2$ in the portion of skin.

In one example, the network is created essentially simultaneously. In another example, the network is created one treatment zone at a time. In another example, the network is created by one pass of a handpiece over the portion of skin during the treating. In yet another example, the network is created by at least two passes of a handpiece over the portion of skin during the treating.

In one example, the treatment zones extend from the surface of the skin through an epidermal layer of the portion of skin and into a dermal layer of the portion of skin. In another example, the treatment zones extend from a lower epidermal layer of the portion of skin into a dermal layer of the portion of skin, leaving at least a layer of the stratum corneum substantially intact.

In one example, tissue within the treatment zones is coagulated. In another example, tissue within the treatment zones is necrosed. In yet another example, tissue within the treatment zones is ablated.

In one example, each of the treatment zones in the network intersects at least one other treatment zone in the network. In another example, the treatment zones intersect at a point below the dermal-epidermal junction of the portion of skin. In yet another example, each of the treatment zones in the network a unique focal point.

In one example, the angles at which the treatment zones are slanted in the portion of skin are between about 10 degrees and about 85 degrees as measured from a line substantially perpendicular to the surface of the portion of skin. In another example, the angles at which the treatment zones are slanted in the portion of skin are between about 45 degrees and about 85 degrees as measured from a line substantially perpendicular to the surface of the portion of skin. In another example, the angles are predetermined. In another example the angles are randomly generated during the treating.

In one example, the skin substantially perpendicularly above the point at which the treatment zones intersect is not treated. In another example, the treating improves the cosmetic appearance of wrinkles in the portion of skin. In yet another example, the method further comprises cooling an epidermal layer of the portion of skin. The epidermal layer can be cooled before, during or immediately following the treating.

The two drawings in FIG. 2 illustrate a network of six slanted, intersecting treatment zones. The drawing in FIG. 2A illustrates a top view of the surface of the skin and shows the tops of the treatment zones (203) at the surface of the skin which are formed by circular treatment beams impacting the surface of the skin. The treatment zones can be formed simultaneously or separately. The drawing in FIG. 2B illustrates a cross-sectional view of this network of treatment zones within the layers of the skin. A treatment beam (201) impacts the surface of the portion of skin (210) and forms a treatment zone (203) in the layers of the skin. As the angle of the treatment beam is acute when measured from a line (207) substantially perpendicular to the surface of the skin (210), the treatment zone (203) created by the beam (201) is similarly angled within the portion of skin. A network of treatment zones are shown in FIG. 2B. The individual treatment zones in the network extend from the surface of the skin (210) through the dermal-epidermal junction of the skin (220) and into the dermal layer of the portion of skin. The individual treatment zones (203) intersect (230) at a point at or below the dermal-epidermal junction of the skin (220). As the treatment zones (201) are slanted, skin substantially perpendicularly above (240) the point of intersection (230) is not treated by the electromagnetic radiation. The network of intersecting treatment zones produces tension (208) within the skin, and results in tightening of the skin.

Figure 3A:
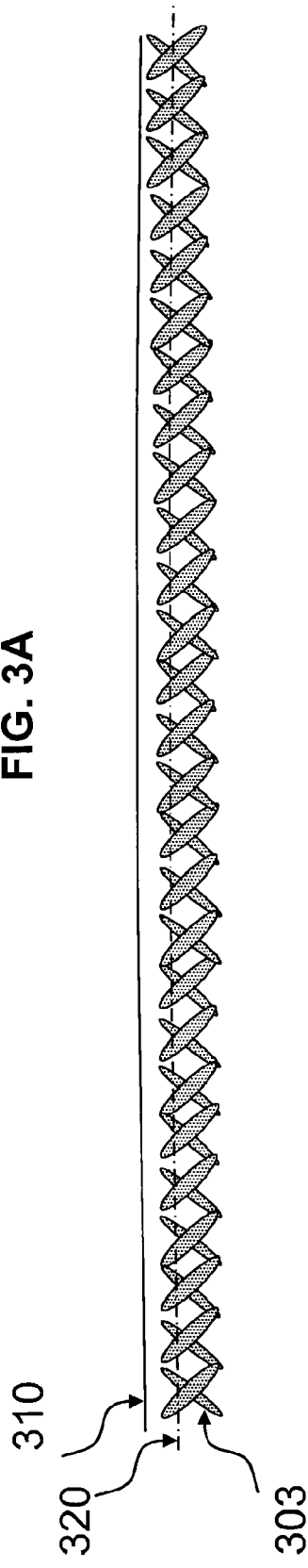
FIG. 3 consist of two cross-sectional drawings illustrating a treatment network of intersecting slanted treatment zones (FIG. 3A) and a treatment network of intersecting slanted and substantially perpendicular treatment zones (FIG. 3B).

The two cross-sectional drawings in FIG. 3 illustrate two different networks of treatment patterns. The drawing in FIG. 3A illustrates a network of 54 treatment zones (303), where the treatment zones are all slanted at angles in the skin and each of the slanted treatment zones intersects at least one other treatment zone in the network. Some of the slanted treatment zones intersect two other treatment zones in the network. The treatment zones begin below the surface of the skin (310), and intersect at a point at or below the dermal-epidermal junction (320) of the region of skin.

Figure 3B:
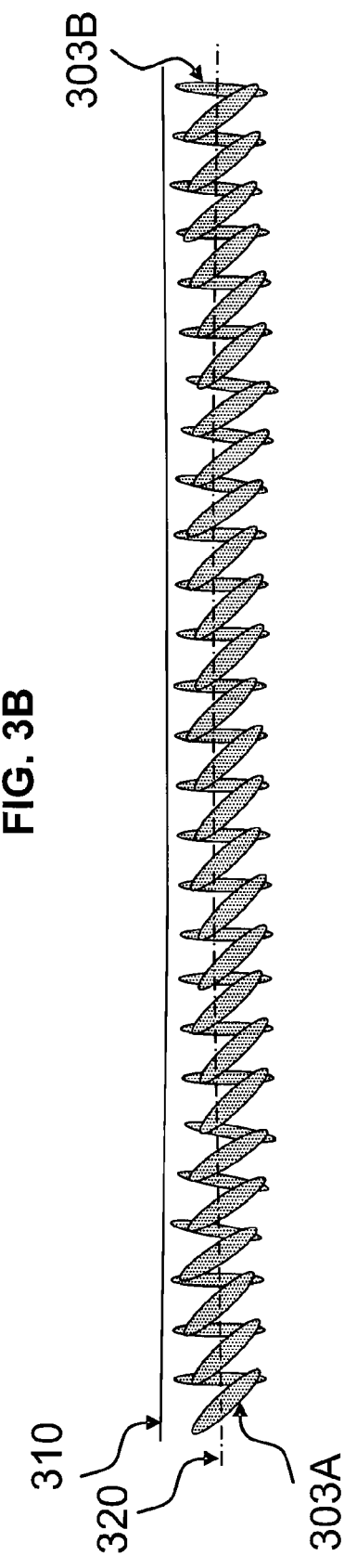

The drawing in FIG. 3B illustrates a network of 54 treatment zones (303), where half the treatment zones are slanted (303A) in the portion of skin and half of the treatment zones are substantially perpendicular (303B) to the surface of the skin (310). The treatment zones begin below the surface of the skin (310). All of the treatment zones (303) intersect at least one other treatment zone in the network; the majority of the treatment zones intersect two other treatment zones in the network. Some of the treatment zones intersect at points within the epidermal layer of the portion of skin, and some of the treatment zones intersect at points below the dermal-epidermal junction (320) of the region of skin.

In some examples, as shown in FIGS. 3A and 3B, the treatment zones can generally lie along a line. By creating a pattern of treatment zones along a line in the tissue, the tissue can be "pulled" with increased tension along that line to cause a directional cinching of the tissue. This can be advantageously used to cause anisotropic tightening within the skin, which can be desirable for example, when lifting the eye brow in a cosmetic treatment of skin that has sagged.

In one example, a method for treating skin comprises treating a portion of skin with electromagnetic radiation in a manner so as to produce a pattern of treatment zones in the portion of skin, wherein the pattern comprises at least four treatment zones, at least two of the treatment zones in the pattern are slanted at angles in the portion of skin, the treatment zones extend at least as deep as a dermal-epidermal junction of the portion of skin, and the treating results in tightening of the portion of skin.

In one example, the pattern comprises at least ten treatment zones. In another example, the pattern comprises at least fifteen treatment zones. In another example, the pattern comprises at least twenty treatment zones. In yet another example, the pattern comprises at least fifty treatment zones.

In another example, the treatment zones comprising the treatment pattern are created essentially simultaneously. In another example, the treatment zones comprising the treatment pattern are created one at a time. In another example, the treatment pattern is predetermined. In another example, the treatment pattern is randomly generated during the treatment. In yet another example, the treatment pattern is repeated in the portion of skin during the treating.

In one example, a first treatment pattern is at least partially overlapped with a second treatment pattern during the treating. In one example, the first and second treatment patterns are the same. In another example, the first and second treatment patterns are different. In yet another example, overlapping the first and second treatment patterns causes at least one treatment zone in the first pattern to intersect at least one treatment zone in the second pattern, wherein the treatment zones intersect at a point below an epidermal layer of the portion of skin. In another example, the treatment zones intersect at a point below the dermal-epidermal junction of the portion of skin.

In one example, the treatment zones extend from a surface of the portion of skin through an epidermal layer of the portion of skin and into a dermal layer of the portion of skin. In another example, the treatment zones extend from a lower epidermal layer of the portion of skin into a dermal layer of the portion of skin, leaving at least a layer of the stratum corneum substantially intact.

In one example, each of the treatment zones in the pattern is slanted. In another example, the slanted treatment zones are angled in the portion of skin such that lines projected along the length of the slanted treatment zones intersect at substantially a single point below the surface of the skin, wherein the treatment zones in the pattern do not extend as deep as the point and do not intersect.

In one example, the angles at which the treatment zones are slanted are between about 10 degrees and about 85 degrees as measured from a line substantially perpendicular to the surface of the portion of skin. In another example, the angles at which the treatment zones are slanted are between about 45 degrees and about 85 degrees as measured from a line substantially perpendicular to the surface of the portion of skin.

In one example, the treating produces a treatment zone density of between about 50 TZ/cm$^2$ and about 2000 TZ/cm$^2$. In another example, the treating produces a treatment zone density of between about 100 TZ/cm$^2$ and about 1000 TZ/cm$^2$.

In one example, the treating improves the cosmetic appearance of wrinkles in the portion of skin. In another example, the method further comprises cooling an epidermal layer of the portion of skin. In another example, the cooling occurs before, during or immediately following the treating.

Figure 4B:
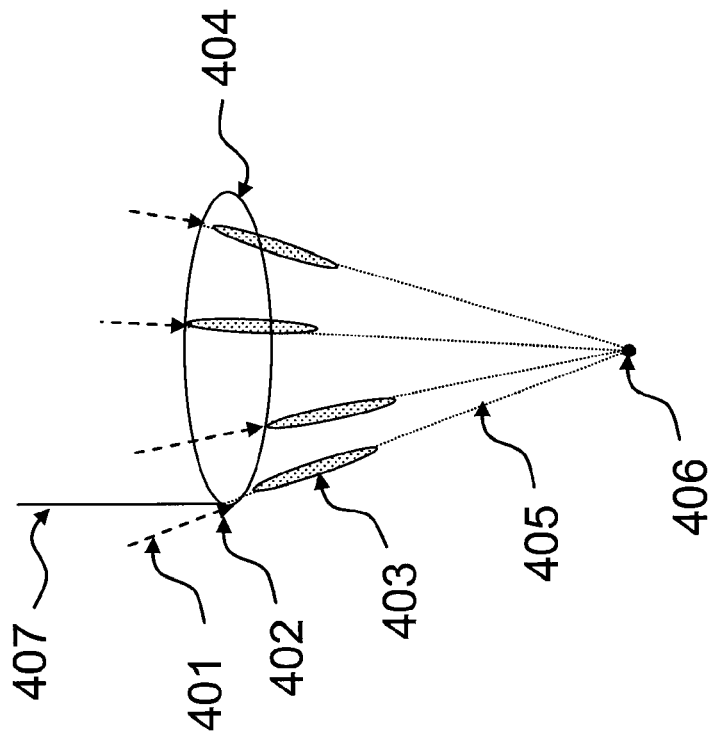
FIG. 4 consists of two drawings, a top-view drawing (FIG. 4A) and a perspective drawing (FIG. 4B) showing a treatment pattern created using four slanted beams of electromagnetic radiation which impact a portion of skin, forming four slanted treatment zones in the epidermal and dermal layers of the skin.
Figure 4A:
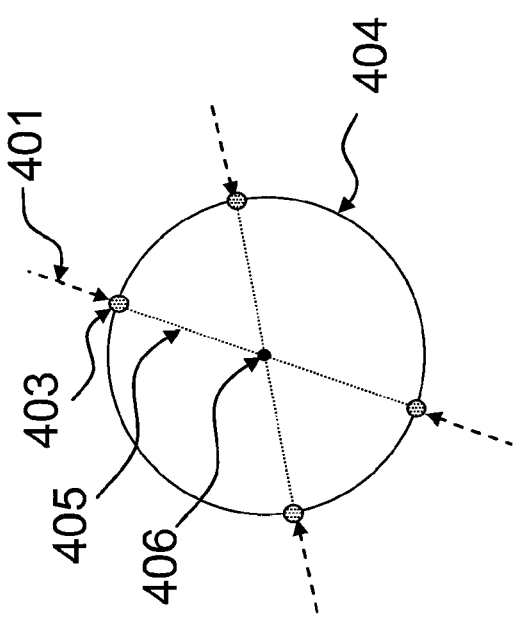

The drawings in FIG. 4 illustrate a top-view (FIG. 4A) and a perspective view (FIG. 4B) of one method of producing a pattern of treatment zones in a portion of skin. In the drawings, the pattern is created using four beams of electromagnetic radiation (401), each of which is aimed at the surface of the skin at different points around the circumference of a circle (404). Similar patterns can be produce using more than four beams, or using a combination of slanted and substantially perpendicular treatment beams. In the example of FIG. 4, each of the four beams is angled such that the beams would substantially converge at a point (406) below the surface of the skin if the beams were to penetrate that deeply into the tissue. Lines (405) indicate the angle of the path of the beams and substantially intersect at a single focal point (406). A line drawn substantially perpendicular to the surface of the skin (407) shows that the angle of the beam (401) is acute with respect to the line (407). The treatment zones (403) are shown on the surface of the skin in the top-view drawing (FIG. 4A) and penetrating at angles into the tissue in the perspective drawing (FIG. 4B). The treatment zones (403) do not penetrate into the tissue as deep as the focal point (406) and thus do not intersect at the focal point (406). By creating a pattern of treatment zones "aimed" in this manner at a point deep in the tissue, the tissue can be "pulled" toward that point, without the need to create extremely deep treatment zones or the need to produce a region of tissue that has been extensively damaged (i.e., a region which has been exposed to radiation from a number of different treatment beams).

The two drawings in FIG. 5 illustrate a perspective view (FIG. 5A) and a cross-sectional view (FIG. 5B) of a pattern of five treatment zones in a portion of skin. Similar patterns can be produce using more than four beams, or using a combination of slanted and substantially perpendicular treatment beams. For example, a number of treatment beams could be directed to the "back" half of the circumference of the ellipse (504). In the example shown in FIG. 5, five treatment beams (501) impact the surface of the skin (510) at five points (502). The five points (502) where the five treatment beams impact the surface (510) of the skin are located on the circumference of an ellipse (504). As each treatment beam (501) impacts the surface of the skin (520) at point (502), it creates a treatment zone (503) below the stratum corneum layer of the epidermis. These treatment zones extend past the dermal-epidermal junction (520) and into the dermal layer of the skin. Due to the angle of each treatment beam (501), each treatment beam (501) creates slanted treatment zone (503) in the portion of skin. Viewed in cross-section, the treatment zones can appear as ellipses, circles or columns, depending upon the angle at which the treatment zone is slanted in the portion of skin and the treatment parameters used.

The two drawings in FIG. 6 illustrate a perspective view (FIG. 6A) and a cross-sectional view (FIG. 6B) of the pattern from FIG. 5 being repeated three times (604U, 604V, 604W) in a portion of skin. In this example, the three patterns (604U, 604V, 604W) are the same and are not overlapped. The treatment zones (603) extend from the surface of the skin (610) through the dermal-epidermal junction (620) and into the dermal layer of the skin.

Figure 7A:
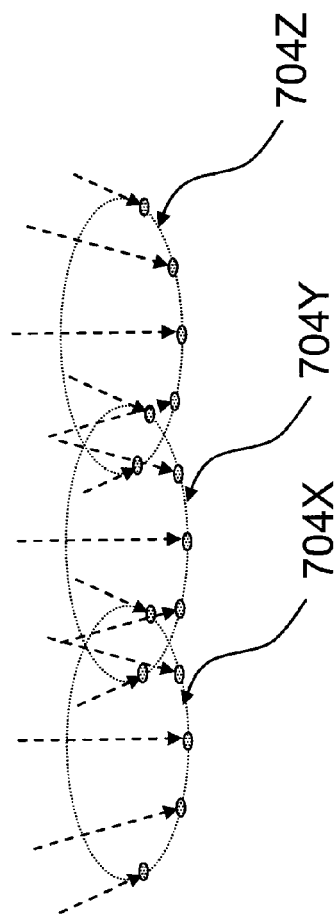
FIG. 7 is composed of two drawings, a perspective view (FIG. 7A) and a cross-sectional view (FIG. 7B) showing three treatment patterns, each containing five beams of electromagnetic radiation, impacting a portion of skin. The three treatment patterns in FIG. 7 are partially overlapped, producing intersecting treatment zones.
Figure 7B:
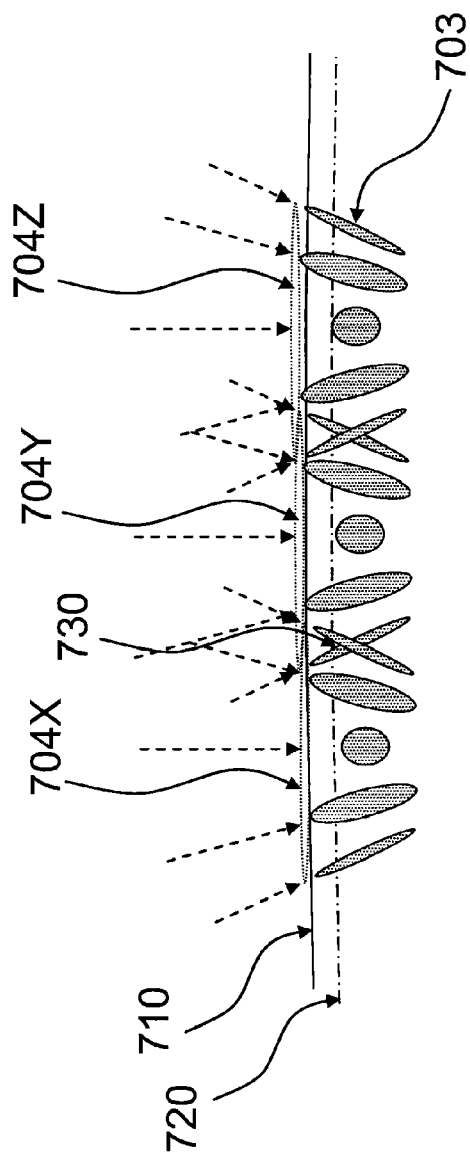

The two drawings in FIG. 7 illustrate a perspective view (FIG. 7A) and a cross-sectional view (FIG. 7B) of the pattern from FIG. 5 being repeated three times (704X, 704Y, 704Z) in a portion of skin. In this example, the three patterns (704X, 704Y, 704Z) are the same and are partially overlapped. The treatment zones (703) extend from the surface of the skin (710) through the dermal-epidermal junction (720) and into the dermal layer of the skin. Due to the overlapping of the patterns, at least one treatment zone (703) from each of the patterns intersects (730) at least one treatment zone from another pattern. The point at which the treatment zones (703) intersect (730) is below the dermal-epidermal junction, and the skin perpendicularly above the point of intersection (730) remains untreated.

The methods for treating skin described herein, which involve creating networks or patterns containing slanted treatments, wherein the treatment zones extend at least as deep as the dermal-epidermal junction, can be accomplished using a number of different devices. In one example, the device comprises a handpiece operably coupled to a delivery element, wherein delivery of electromagnetic radiation through the device to a portion of skin produces a network of at least four treatment zones, at least two of the treatment zones are slanted at angles in the portion of skin, the treatment zones extend at least as deep as a dermal-epidermal junction of the portion of skin, and at least one of the treatment zones intersects another treatment zone in the network. In one example, the treatment zones intersect at a point below an epidermal layer of the portion of skin. In another example, the treatment zones intersect at a point below the dermal-epidermal junction of the portion of skin. In yet another example, skin substantially perpendicularly above the point at which the treatment zones intersect is not treated.

In another example, the device comprises a handpiece operably coupled to a delivery element, wherein delivery of electromagnetic radiation through the device to a portion of skin produces a pattern of at least four treatment zones, at least two of the treatment zones in the pattern are slanted at angles in the portion of skin, and the treatment zones extend at least as deep as a dermal-epidermal junction of the portion of skin In another example, all of the treatment zones in the pattern are slanted at angles in the portion of skin. In another example, the slanted treatment zones in the pattern are slanted at angles such that lines projected along the length of each treatment zone intersect at substantially a single point below an epidermal layer of the portion of skin, wherein the treatment zones in the pattern do not extend as deep as the point and do not intersect.

In one example, the delivery element of the device comprises an array of optical fibers configured to deliver beams of electromagnetic radiation at a variety of angles. In another example, the delivery element comprises a scanner operably coupled to a lens. In another example, the scanner comprises a rotating scanner. In another example, the scanner comprises a starburst scanner. In another example, the scanner is capable of creating beams of electromagnetic radiation at different angles. In another example, the scanner comprises a 2-dimensional scanner and the lens comprises a lens with a numerical aperture between about 0.25 and about 1.4. In another example, the scanner comprises a 1-dimensional scanner and the lens comprises a cylindrical lens, wherein the scanner and the axis of the lens are not aligned. In yet another example, the scanner comprises two galvanometer scanners.

In one example, the electromagnetic radiation is continuous. In another example, the electromagnetic radiation is pulsed. In one example, delivery of electromagnetic radiation through the device to a portion of skin results in multiple beams of electromagnetic radiation being directed to the surface of the skin as the device is moved across the skin. In another example, delivery of electromagnetic radiation through the device to a portion of skin results in multiple beams of electromagnetic radiation being directed to the surface of the skin as the device is placed at multiple location on the surface of the skin.

In one example, delivery of electromagnetic radiation through the device to the portion of skin produces tightening of the portion of skin. In another example, the device is used to improve the cosmetic appearance of skin. In yet another example, the device is used to improve the cosmetic appearance of wrinkles in the portion of skin.

In one example, the device further comprises a cooling means. In one example, the cooling means comprises a cooling surface. In another example, the cooling means comprises a sprayer which dispenses a cooling liquid. In another example, the cooling means comprises a surface cooled using a liquid.

Figure 8:
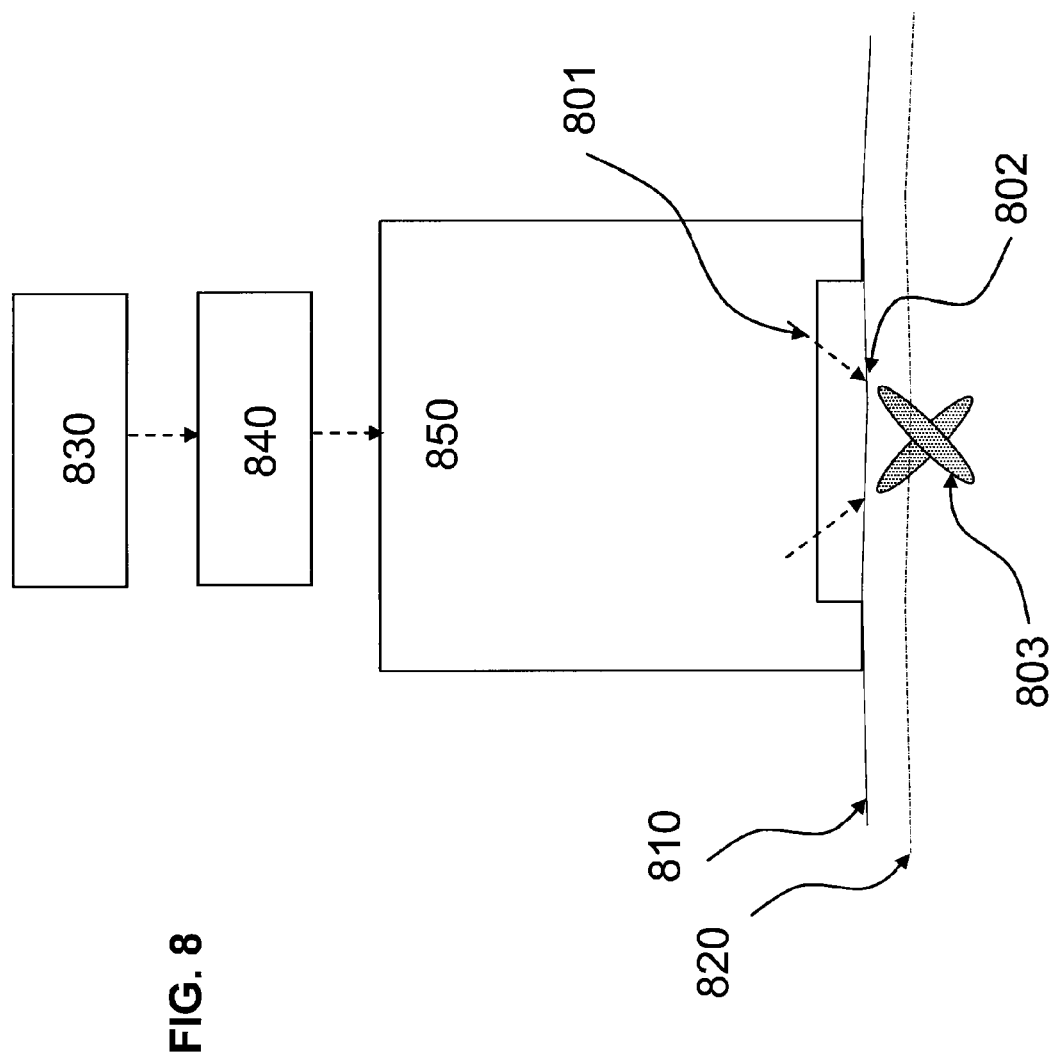
FIG. 8 is a cross-sectional drawing illustrating a device for treating skin which can be used to produce slanted, intersecting treatment zones in a portion of skin.

FIG. 8 is a cross-sectional drawing which illustrates a device for treating skin using electromagnetic radiation. It includes a handpiece (850) operable coupled to a delivery element (840). The delivery element (840) can optionally be located inside the handpiece. A source of electromagnetic radiation (830) can optionally be operably coupled to the delivery element (840). When the handpiece (850) is placed in contact with the surface of a portion of skin (810), beams of electromagnetic energy (801) can be directed through the delivery element and through the handpiece to impact the surface of skin (810) at a point (802) and create a treatment zone (803) in the portion of skin. This device can be used to create networks of treatment zones containing slanted treatment zones (803) which intersect below the dermal-epidermal junction (820). It can also be used to create patterns of treatment zones containing slanted treatment zones which penetrate at least as deep as the dermal-epidermal junction (820). This device can be used for cosmetic and/or medical purposes, such as to treat wrinkles and to tighten skin.

FIG. 9 is a cross-sectional drawing which illustrates another device for treating skin using electromagnetic radiation. It includes a handpiece (950) operably coupled to a delivery element (940). The delivery element (940) can, for example, be a collimating or focusing lens assembly. The delivery element (940) can optionally be located in the handpiece (950). In this example, the handpiece contains a mirror (960) and a starburst scanner (970). Starburst scanners are described generally in copending U.S. patent application Ser. No. 11/158,907. The starburst scanner (970) pictured in FIG. 9 includes facets that are not perpendicular to the plane of the paper. These facets are used to create a two dimensional pattern of beams on the surface of a focusing lens (980). Appropriate curvature can be added to the facets as desired for focusing or translating the beams. The device can be used to create a pattern of treatment zones in a portion of skin when electromagnetic radiation passes through the delivery element (940) and the handpiece (950) to a surface of a portion of skin (910). The beam of electromagnetic radiation (901) passes from the delivery element (940) into the handpiece (950) and is deflected by the mirror (960) onto a first facet of the starburst scanner (970), where it is again deflected off a second facet of the starburst scanner (970) and then passes through a lens (980) before impacting the surface of the skin (910). The facets of the starburst scanner are angled such that as the beam (901) impacts the facet, it is deflected at an angle. The different facets of the scanner can have different angles, resulting in the beam being deflected at different angles as the scanner rotates. Beam (901A) represents a beam that has been deflected in front of the plane of the drawing, while beams (901B) and (901C) represent beams that have not been deflected out of the plane of the drawing. In this manner, the beam can be deflected, creating points of impact on the surface of the skin in a particular shape, such as, for example, around the circumference of a circle or ellipse. Additional facet pairs in the starburst scanner can deflect the beam to other points in a circle near the perimeter of the lens (980). This arrangement can thus be used to create lesions as depicted, for example, in FIGS. 4A and 4B. In the example, the beams pass through a lens (980) before impacting the surface of the skin (910) and producing treatment zones (903) in the portion of skin. Due to the deflection of the treatment beam (901C, 901D) at different angles, some or all of the treatment zones (903) can be slanted at angles in the portion of skin. Alternatively, the delivery element (940) can deliver the beam (901) to a pair of galvanometer scanners that are configured to reflect the beam (901) to the lens (980). The galvanometer pair can be arranged such that one galvanometer deflects the beam in the "x-direction" on the skin and the other deflects the beam in the "y-direction" on the skin, thus allowing the selection of any 2 dimensional pattern desired on the focusing lens (980). This configuration can thus be used to create a pattern of treatment zones such as the ones shown in FIGS. 4, 5, and 9. These devices can be used for cosmetic and/or medical purposes, such as to treat wrinkles and to tighten skin.

Various forms of electromagnetic radiation can be used in accordance with the methods and devices described herein, including ultraviolet radiation, visible light, infrared radiation, radar, and radio waves. The electromagnetic radiation can be coherent in nature, such as laser radiation, or non-coherent in nature, such as flash lamp radiation. The coherent electromagnetic radiation can be produced by one or more lasers, including gas lasers, dye lasers, metal-vapor lasers, and/or solid-state lasers. The laser can be ablative or nonablative. The type of lasers used in accordance with this invention can be selected from the group consisting of an argon ion gas laser, a carbon dioxide ($CO_2$) gas laser, an excimer chemical laser, a dye laser, a neodymium yttrium aluminum garnet (Nd:YAG) laser, an erbium yttrium aluminum garnet (Er:YAG) laser, a holmium yttrium aluminum garnet (Ho:YAG) laser, an alexandrite laser, an erbium doped glass laser, a neodymium doped glass laser, a thulium doped glass laser, an erbium-ytterbium co-doped glass laser, a fiber laser, an erbium doped fiber laser, a neodymium doped fiber laser, a thulium doped fiber laser, an erbium-ytterbium co-doped fiber laser, and combinations thereof.

In one example, the wavelength of the laser radiation can be a wavelength that is absorbed within the skin primarily by water, such as, for example, the wavelengths between about 1300 nanometers (nm) and about 12,000 nm. Depending on the desired depth of treatment and desired treatment zone size, the wavelength of the laser radiation used can be selected from the group consisting of between about 1250 nm and about 2500 nm, between about 1280 nm and about 1350 nm, between about 1400 nm and about 1500 nm, between about 1500 nm and about 1620 nm, between about 1780 nm and 2000 nm, and combinations thereof. Wavelengths longer than 1500 nm can be used if the goal is to get deep penetration with small treatment zones. The shorter wavelengths generally have higher scattering coefficients than the longer wavelengths.

The spot size of a treatment beam is the size of the beam of electromagnetic radiation at the point when it hits the surface of the target tissue, and is measured based on the cross-sectional width or diameter of the beam. Spot size can be selected based on the desired depth of the treatment zone and/or the desired healing time for the treatment zone. In accordance with this invention, the spot size can be selected from the group consisting of between about 0.5 μm and about 500 μm, between about 1 μm and about 360 μm, between about 1 μm and about 250 μm, between about 1 μm and about 180 μm, about 60 μm, and about 140 μm.

The treatment zone density is the number of treatment zones that are created within the portion of tissue undergoing treatment. Treatment zone density can be selected based on the aggressiveness of the treatment desired. The treatment zone density can also be selected in conjunction with the spot size so as to achieve a desired "fill factor" of treatment zones within a volume of tissue. The treatment zone density can be selected in conjunction with the treatment zone angle and depth to ensure treatment zones intersect each other. The treatment zone density can also be selected based on the number of intersecting treatment zones and/or overlapping treatment patterns desired, as increasing the density can increase the number of intersecting treatment zones and/or overlapping treatment patterns. When expressed as a fill factor, the treatment zone density can be between about 0.05 and about 0.95, or between about 0.1 and about 0.5. When expressed as the number of treatment zones created in a region of skin, the treatment zone density can be selected from the group consisting of between about 100 and 10,000 treatment zones per square centimeter ($TZ/cm^2$), between about 100 and about 2000 $TZ/cm^2$, between about 100 and about 1000 $TZ/cm^2$, and between about 100 and about 500 $TZ/cm^2$ of treated region of tissue.

While a major focus of the methods and devices described herein is tightening the skin and improving the cosmetic appearance of wrinkles, these methods and devices are suitable for treatment of a variety of biological tissues in addition to skin. Other biological tissues which can be treated with these methods and devices include tissues with structures similar to human skin, such as, for example, tissues that have an epithelium and underlying structural tissues, such the soft palate.

Similarly, while these methods and devices can be used for cosmetic or medical purposes to remodel tissue (for example, for collagen remodeling), to resurface tissue, and/or to treat wrinkles and photoaging of the skin, they are also suitable to treat a variety of dermatological condition such as hypervascular lesions including port wine stains, capillary hemangiomas, cherry angiomas, venous lakes, poikiloderma of civate, angiokeratomas, spider angiomas, facial telangiectasias, telangiectatic leg veins; pigmented lesions including lentigines, ephelides, nevus of Ito, nevus of Ota, Hori's macules, keratoses pilaris; acne scars, epidermal nevus, Bowen's disease, actinic keratoses, actinic cheilitis, oral florid papillomatosis, seborrheic keratoses, syringomas, trichoepitheliomas, trichilemmomas, xanthelasma, apocrine hidrocystoma, verruca, adenoma sebacum, angiokeratomas, angiolymphoid hyperplasia, pearly penile papules, venous lakes, rosacea, etc. While specific examples of dermatological conditions are mentioned above, it is contemplated that these methods and devices can be used to treat virtually any type of dermatological condition. Additionally, these methods and devices can be applied to other medical specialties besides dermatology.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

All publications, patents and patent applications cited herein, whether supra or infra, are hereby incorporated by reference in their entirety.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

What is claimed is:

1. A method for treating skin, the method comprising:
   delivering electromagnetic radiation at an acute angle relative to a first line substantially perpendicular to the surface of a portion of skin;
   treating the portion of skin with the electromagnetic radiation in a manner so as to create a network of treatment zones in the portion of skin,
   wherein the network comprises at least four treatment zones, at least two of the treatment zones in the network are slanted at angles between a second line projected along a length of each slanted treatment zone and the first line, the treatment zones extend at least as deep as a dermal-epidermal-junction of the portion of skin, at least one of the treatment zones in the network intersects another treatment zone at a point below an epidermal layer of the portion of skin, and the treating results in tightening of the portion of skin.

2. The method of claim 1, wherein the network comprises at least twenty treatment zones.

3. The method of claim 1, wherein the network comprises at least fifty treatment zones.

4. The method of claim 1, wherein the network has a treatment zone density of between about 50 treatment zones/cm$^2$ and about 2000 treatment zones/cm$^2$ in the portion of skin.

5. The method of claim 1, wherein the network is created by at least two passes of a handpiece over the portion of skin during the treating.

6. The method of claim 1, wherein the treatment zones extend from a surface of the portion of skin through an epidermal layer and into a dermal layer of the portion of skin.

7. The method of claim 1, wherein the treatment zones extend from a lower epidermal layer of the portion of skin into a dermal layer of the portion of skin, leaving at least a layer of stratum corneum substantially intact.

8. The method of claim 1, wherein tissue within the treatment zones is ablated.

9. The method of claim 1, wherein each of the treatment zones intersects at least one other treatment zone in the network.

10. The method of claim 1, wherein the treatment zones intersect at a point below the dermal-epidermal junction of the portion of skin.

11. The method of claim 1, wherein each of the treatment zones has a unique focal point.

12. The method of claim 1, wherein the angles are predetermined.

13. The method of claim 1, wherein the angles are randomly generated during the treating.

14. The method of claim 1, wherein skin substantially perpendicularly above the point at which the treatment zones intersect is not treated.

15. The method of claim 1, wherein the treating improves the cosmetic appearance of wrinkles in the portion of skin.

16. The method of claim 1, wherein the method further comprises cooling of an epidermal layer of the portion of skin before, during or immediately following the treating.

17. A method for treating skin, the method comprising:
   delivering electromagnetic radiation at an acute angle relative to a first line substantially perpendicular to the surface of a portion of skin;
   treating the portion of skin with the electromagnetic radiation in a manner so as to produce a pattern of treatment zones in the portion of skin,
   wherein the pattern comprises at least four treatment zones, at least two of the treatment zones in the pattern are slanted at angles between a second line projected along a length of each slanted treatment zone and the first line, the treatment zones extend at least as deep as a dermal-epidermal-junction of the portion of skin, and the treating results in tightening of the portion of skin.

18. The method of claim 17, wherein the pattern comprises at least ten treatment zones.

19. The method of claim 17, wherein the pattern comprises at least fifteen treatment zones.

20. The method of claim 17, wherein the pattern is predetermined.

21. The method of claim 17, wherein the pattern is randomly generated during the treating.

22. The method of claim 17, wherein the pattern is repeated in the portion of skin during the treating.

23. The method of claim 17, wherein a first pattern is at least partially overlapped with a second pattern during the treating.

24. The method of claim 23, wherein at least partially overlapping the first and second patterns causes at least one treatment zone in the first pattern to intersect at least one treatment zone in the second pattern, and wherein the treatment zones intersect at a point below an epidermal layer of the portion of skin.

25. The method of claim 24, wherein the treatment zones intersect at a point below the dermal-epidermal junction of the portion of skin.

26. The method of claim 17, wherein the treatment zones extend from a surface of the portion of skin through an epidermal layer and into a dermal layer of the portion of skin.

27. The method of claim 17, wherein the treatment zones extend from a lower epidermal layer of the portion of skin into a dermal layer of the portion of skin, leaving at least a layer of stratum corneum substantially intact.

28. The method of claim 17, wherein each of the treatment zones in the pattern is slanted.

29. The method of claim 17, wherein the at least two slanted treatment zones in the pattern are slanted at angles such that lines projected along the length of each treatment zone intersect at substantially a single point below a surface of the portion of skin, wherein the treatment zones in the pattern do not extend as deep as the point and do not intersect.

30. The method of claim 17, wherein the treating produces a treatment zone density of between about 50 treatment zones/cm$^2$ and about 2000 treatment zones/cm$^2$ in the portion of skin.

31. The method of claim 17, wherein the treating improves the cosmetic appearance of wrinkles in the portion of skin.

32. The method of claim 17, wherein the method further comprises cooling of an epidermal layer of the portion of skin before, during or immediately following the treating.

33. A device for treating skin, comprising:
   a handpiece operably coupled to a delivery element,
   wherein the delivery element is configured to deliver electromagnetic radiation at an acute angle relative to a first line substantially perpendicular to the surface of a portion of skin and the electromagnetic radiation produces a network of at least four treatment zones,
   wherein at least two of the treatment zones in the network are slanted at angles between a second line projected along a length of each slanted treatment zone and the first line, the treatment zones extend at least as deep as a dermal-epidermal junction of the portion of skin, and at least one of the treatment zones in the network intersects another treatment zone in the network.

34. The device of claim 33, wherein the treatment zones intersect at a point below an epidermal layer of the portion of skin.

35. The device of claim 33, wherein the treatment zones intersect at a point below the dermal-epidermal junction of the portion of skin.

36. The device of claim 34, wherein skin substantially perpendicularly above the point at which the treatment zones intersect is not treated.

37. A device for treating skin, comprising:
   a handpiece operably coupled to a delivery element,
   wherein the delivery element is configured to deliver electromagnetic radiation at an acute angle relative to a first line substantially perpendicular to the surface of a portion of skin and the electromagnetic radiation produces a pattern of at least four treatment zones,
   wherein at least two treatment zones in the pattern are slanted at angles between a respective second line projected along a length of each slanted treatment zone and the first line, and the treatment zones extend at least as deep as a dermal-epidermal junction of the portion of skin, and wherein the angles of the at least two of the treatment zones are between about 45 degrees and about 85 degrees.

38. The device of claim 37, wherein all of the treatment zones in the pattern are slanted at angles in the portion of skin.

39. The device of claim 37, wherein the angles are such that lines projected along the length of each slanted treatment zone intersect at substantially a single point below an epidermal layer of the portion of skin, and wherein the treatment zones in the pattern do not extend as deep as the point and do not intersect.

40. The device of claim 33 or 37, wherein the delivery element comprises an array of optical fibers configured to deliver beams of electromagnetic radiation at a variety of angles.

41. The device of claim 33 or 37, wherein the delivery element comprises a scanner operably coupled to a lens.

42. The device of claim 41, wherein the scanner comprises a rotating scanner.

43. The device of claim 41, wherein the scanner is capable of creating beams of electromagnetic radiation at different angles.

44. The device of claim 41, wherein the scanner comprises a 2-dimensional scanner and the lens comprises a lens with a numerical aperture between about 0.25 and about 1.4.

45. The device of claim 41, wherein the scanner comprises a 1-dimensional scanner and the lens comprises a cylindrical lens, and wherein the scanner and the axis of the lens are not aligned.

46. The device of claim 33 or 37, wherein the electromagnetic radiation is continuous.

47. The device of claim 33 or 37, wherein the electromagnetic radiation is pulsed.

48. The device of claim 33 or 37, wherein delivery of electromagnetic radiation through the device to a portion of skin results in multiple beams of electromagnetic radiation being directed to the surface of the skin as the device is moved across the surface of the skin.

49. The device of claim 33 or 37, wherein delivery of electromagnetic radiation through the device to a portion of skin results in multiple beams of electromagnetic radiation being directed to the surface of the skin as the device is placed at multiple locations on the surface of the skin.

50. The device of claim 33 or 37, wherein delivery of electromagnetic radiation through the device to the portion of skin produces tightening of the portion of skin.

51. The device of claim 33 or 37, wherein delivery of electromagnetic radiation through the device to the portion of skin is used to improve the cosmetic appearance of wrinkles.

52. The device of claim 33 or 37, further comprising a cooling surface.

* * * * *

UNITED STATES PATENT AND TRADEMARK OFFICE
CERTIFICATE OF CORRECTION

PATENT NO. : 8,323,253 B2  
APPLICATION NO. : 12/035956  
DATED : December 4, 2012  
INVENTOR(S) : Basil M. Hantash et al.

It is certified that error appears in the above-identified patent and that said Letters Patent is hereby corrected as shown below:

In the Claims:

Column 22, claim number 1, line number 60, before "second", insert --respective-- and at line number 67, after "skin" insert --, wherein the angles of the at least two of the treatment zones are between about 45 degrees and about 85 degrees--.

Column 23, claim number 17, line number 50, before "second", insert --respective-- and at line number 54, after "skin" insert --, wherein the angles of the at least two of the treatment zones are between about 45 degrees and about 85 degrees--.

Column 24, claim number 33, line number 43, before "second", insert --respective-- and at line number 48, after "network", insert --, wherein the angles of the at least two of the treatment zones are between about 45 degrees and about 85 degrees--.

Signed and Sealed this  
Seventh Day of May, 2013

Teresa Stanek Rea  
*Acting Director of the United States Patent and Trademark Office*